United States Patent [19]

Geisslinger et al.

[11] Patent Number: 5,565,613

[45] Date of Patent: Oct. 15, 1996

[54] 2-ARYLPROPIONIC ACID PREPARATIONS AND PROCESS FOR THEIR PRODUCTION

[75] Inventors: Gerd Geisslinger, Nuremberg; Kay Brune, Marloffstein; Kurt Bauer, Freiburg, all of Germany; Anton S. Huber, Basel, Switzerland

[73] Assignee: Pharmatrans Sanaq AG, Basel, Switzerland

[21] Appl. No.: 338,451

[22] PCT Filed: May 19, 1993

[86] PCT No.: PCT/EP93/01243

§ 371 Date: Nov. 21, 1994

§ 102(e) Date: Nov. 21, 1994

[87] PCT Pub. No.: WO93/23026

PCT Pub. Date: Nov. 25, 1993

[30] Foreign Application Priority Data

May 21, 1992 [DE] Germany .......................... 42 16 756.6

[51] Int. Cl.⁶ .................................................. C07C 53/134
[52] U.S. Cl. ........................ 562/496; 424/464; 424/465; 424/490; 424/492; 424/494; 424/497
[58] Field of Search .............. 562/496; 424/464, 424/465, 490, 492, 494, 497; 514/568

[56] References Cited

U.S. PATENT DOCUMENTS 4,873,231  10/1989  Smith ........................................ 514/557

FOREIGN PATENT DOCUMENTS 0241615  10/1987  European Pat. Off. .
0295212  12/1988  European Pat. Off. .
3922441  1/1991  Germany .

*Primary Examiner*—Paul J. Killos
*Attorney, Agent, or Firm*—Foley & Lardner

[57] ABSTRACT

The present invention concerns a process for the production of compositions of 2-arylpropionic acid derivatives with improved tablettability which contain per se known adjuvant and/or carrier materials, whereby the arylpropionic acid is mixed with a calcium compound and, after addition of the remaining adjuvant and/or carrier materials, is pressed to tablets, as well as pharmaceutical compositions produced therewith.

19 Claims, 2 Drawing Sheets

2-ARYLPROPIONIC ACID PREPARATIONS AND PROCESS FOR THEIR PRODUCTION

This application is filed under 35USC 371 of PCT/EP93/01243 filed May 19, 1993.

The invention concerns new preparations of 2-arylpropionic acids with improved tablettability and improved strength which, in particular, contain ibuprofen racemate, S-ibuprofen or mixtures of R- and B-ibuprofen, as well as usual adjuvant and/or carrier materials, as well as processes for their production.

2-Arylpropionic acid derivatives, such as ibuprofen, flurbiprofen, ketoprofen, tiaprofen or pirprofen, as well as their enantiomers, are used in therapy as non-steroidal antiphlogistics, anti-rheumatics, analgesics or antipyretics.

From technological point of view, these medicaments possess disadvantages. They are only poorly soluble in water and possess relatively low melting ranges. Thus, e.g. ibuprofen melts at about 75°–77° C., the flurbiprofen racemete at about 110°–111° C. and the ketoprofen racemate at about 94° C. The enantiomers of ibuprofen even already melt at about 50° C.

As is known, materials with low melting range lead, in the case of the tabletting as a result of sintering occurrences and due to adhesion to the stamps and matrices of the tabletting presses, to more or less strongly disturbing production problems (H. Sucker, P. Fuchs and P. Speiser: Pharmazeutische Technologie, Georg Thieme Verlag, Stuttgart 1978, p. 381).

The adhesion of these low melting medicaments can be removed by admixture of large amounts of anti-adhesives (mould separation agents). However, the mixtures thereby become hydrophobic. From this in turn results a delayed liberation of the medicament, involved with a delayed resorption or even poor bioavailability. As a result of overdosing of the anti-adhesive, the tablets can also become too soft.

Up to a certain extent, the complications in the case of the tablet production can be overcome by the addition of certain tabletting adjuvant materials, such as anti-adhesives or lubricants, in comparatively high doses, as well as by a drastic reduction of the rate of pressing. Furthermore, according to experience, in the case of tablets which contain low melting ingredients, after certain storage times, there is to be reckoned with post-hardenings as a result of sinterings (K. H. Bauer, K. H. Frömming and C. Führer: Pharmazeutische Technologie, Georg Thieme Verlag, Stuttgart, New York, 1986). These post-hardenings bring with them impairments of the breakdown time and not sufficient medicament liberations or not sufficient bio-availabilities.

Hitherto, a tabletting of 2-arylpropionic acids was attempted with varying successs to remove these disadvantages by addition of mould separating or lubricating agents, drying agents (e.g. highly dispersed silicic acid), suitable filling agents and of strong breakdown accelerators (e.g. Kollidon CL®, cross-linked PVP), above all, however, by more than average increases of the added amounts of these adjuvant materials.

In the European Patent Application EP-A-O 267 321 is described an ibuprofen-containing medicament which contains ibuprofen only in the S(+)-form. However, this known medicament possesses the above-mentioned disadvantages, i.e. it can only be poorly tabletted.

The sintering or melting together can also be prevented by addition of comparatively large amounts of filling agent, for example cellulose powder or lactose, or by means of disintegration agents, for example starch. However, too high additions of disintegration agent most result in soft tablets with increased friability since starch or other similarly elastic materials alone or in high dosaging can only be poorly compressed or the tablets become so large that they can only be swallowed with difficulty.

In the German Patent Application P 39 22 441.4 is described a process to improve the tablettability of ibuprofen and S(+)-ibuprofen. It was found that when ibuprofen or S(+)-ibuprofen are converted wholly of partly into their calcium salts and these are used for the tablet production, the tablettability can be clearly improved. Already 25% of calcium salt of the corresponding ibuprofen noticeably improve the tabletting properties but 50 to 100% are preferred. Furthermore, the remaining part of the ibuprofen can be converted into the also higher melting sodium or ammonium salts. The conversion of the ibuprofen into the calcium salt takes place by reaction with an aqueous solution of $Ca(OH)_2$ or of s soluble calcium salt. This reaction is preferably carried out in the case of the granulation process. This process displays two disadvantages:

1. The conversion of the ibuprofen into the calcium salt during the granulation is laborious and technically not easy to carry out. The considerable amounts of aqueous solution must be evaporated off.

2. Compared with other ibuprofen salts, calcium ibuprofenate is sparingly soluble in water. Thus, especially when the portion of calcium ibuprofenate in the medicament is very high, one must reckon with negative properties with regard to breakdown, active material liberation and bioavailability. Thus, positive tabletting properties are obtained with disadvantages with regard to the pharmacokinetics. Because of the high dosaging in the base formulation, e.g. of the Ca—Na glycinate, which is added thereto in molar amounts, very hard tablets result which, in part, showed breakdown times of up to 3 hours.

Now the present invention is based upon the task of making available compositions with improved tablettability, improved strength and improved liberation containing 2-arylpropionic acids or their enantiomers, especially an ibuprofen, S- or R-ibuprofen or mixtures of both enantiomers, as well as a simple economic process for their production.

This task is solved or promoted by the features described in the claims.

Surprisingly, it was found that even in the case of the dry mixing of 100 parts by weight of ibuprofen or of other 2-arylpropionic acids with about 50–500 parts by weight, preferably 50–150 parts by weight of calcium compounds (e.g. $CaHPO_4$, $CaCO_3$, $Ca(OH)_2$ etc.), i.e. approximately equimolar amounts, without problems surprisingly well flowable and complication-free tabelettable powder mixtures result. Especially good tabelletting properties were achieved when $CaH(PO_4)$ was used as calcium compound. In the case of the dry mixing together of e.g. ibuprofen with other adjuvant materials usually employed in tabletting (e.g. microcrystalline cellulose, see EP-A-O 267 321, page 4, Example 1), this is not the case (see enclosure). Such mixtures show the described disadvantages in the case of the tabletting. The differences in the flow behaviour are shown by the natural angle of repose of the powder of 23°–27° in the case of products according to the invention in comparison with 38°–40° in the case of mixtures e.g. with microcrystalline cellulose.

Furthermore, it was, surprisingly, found that by means of the usual addition of Mg stearate or Ca stearate, the experimental batch easily became sticky and thus was difficult to tablet. The proportion of such anti-adhesive agents or mould separating agents could, contrary to conventional formulations, e.g. in the case of ibuprofen (EP-A-O 267 321) or R-flurbiprofen (DE-A-4028 906), be reduced or such additive materials completely omitted.

Thus, the present invention concerns a process with which can be produced forms of medicaments containing arylpropionic acid derivatives or their enantiomers or mixtures with substantial omission of lubricating agent or mould separation agent which act negatively on the galenical or pharmacokinetic properties of the formulation.

In the case of the dry mixing and tabletting of 2-arylpropionic acids with the calcium compounds according to the invention, in contradistinction to the process of moist granulation according to DE-A-3 922 41.4, there result the sparingly soluble calcium salts in small amount, preferably of 0.1–5%, so that the solubility and accordingly the speed of liberation of the arylpropionic acid is not reduced. This can easily be demonstrated by extraction of the tablets with organic solvents in which the free propionic acid but not the corresponding calcium salts are soluble.

Furthermore, preferred compositions contain a wetting agent, such as e.g. Na lauryl sulphate, Tween, Na dioctylsulphosuccinate, or another usual wetting agent in low dosaging, 0.1 to 3% being preferred, whereby the rate of liberation is improved. Furthermore, additional usual adjuvant and/or carrier materials can naturally be contained therein.

The following Examples describe some formulations according to the invention without limiting the invention.

EXAMPLE 1

S-ibuprofen oblong tablets
1 tablet contains:

| | |
|---|---|
| S-ibuprofen (about 99% optical purity) | 300 mg |
| Emcompress (CaH(PO$_4$)) | 240 mg |
| Explotab (disintegration agent) | 14 mg |
| Aerosil R 972 (silica gel) | 6 mg |

The substances are taken and brought together dry and subsequently forced through an e.g. 0.8 mm sieve and pressed on s usual matrix tablet press. A lumping or caking on of the mass was observed neither in the conveying pipes nor in the matrices. The tablets display, in the case of good hardness, a rapid disintegration in water and a rapid liberation of the active material.

EXAMPLE 2

Figure 1:
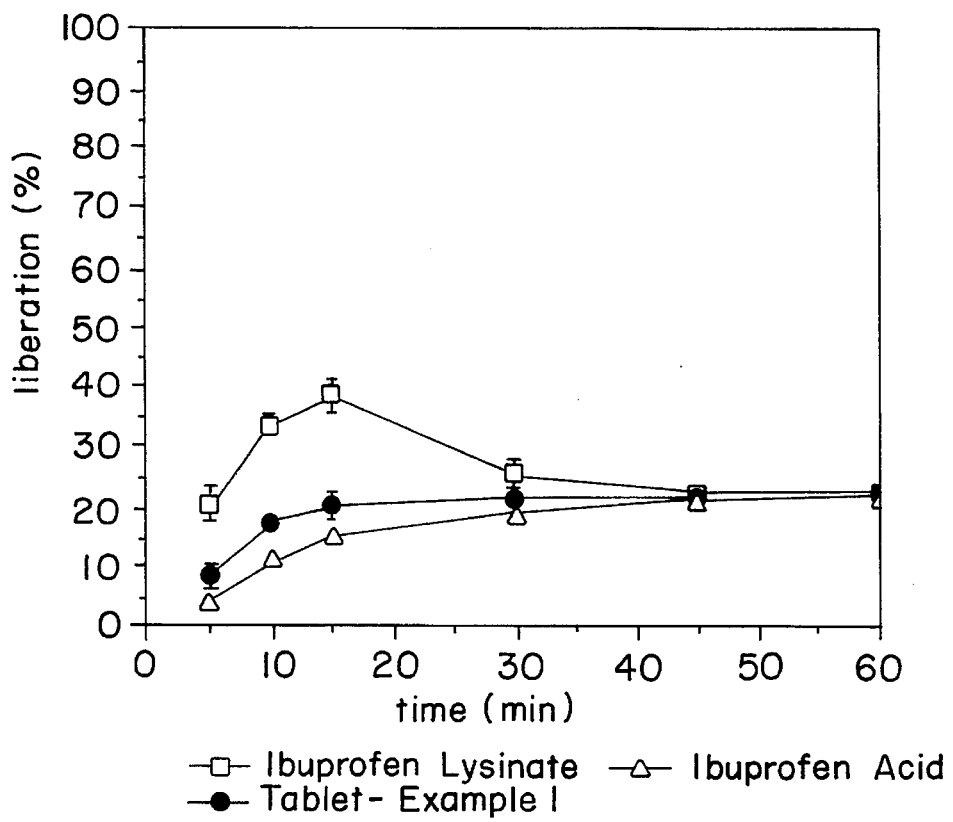
In FIGS. 1 and 2 is compared the in vitro liberation of the tablet according to the invention with 2 commercially available formulations which contain ibuprofen lysinate or ibuprofen acid and known adjuvant and carrier materials.
Figure 2:
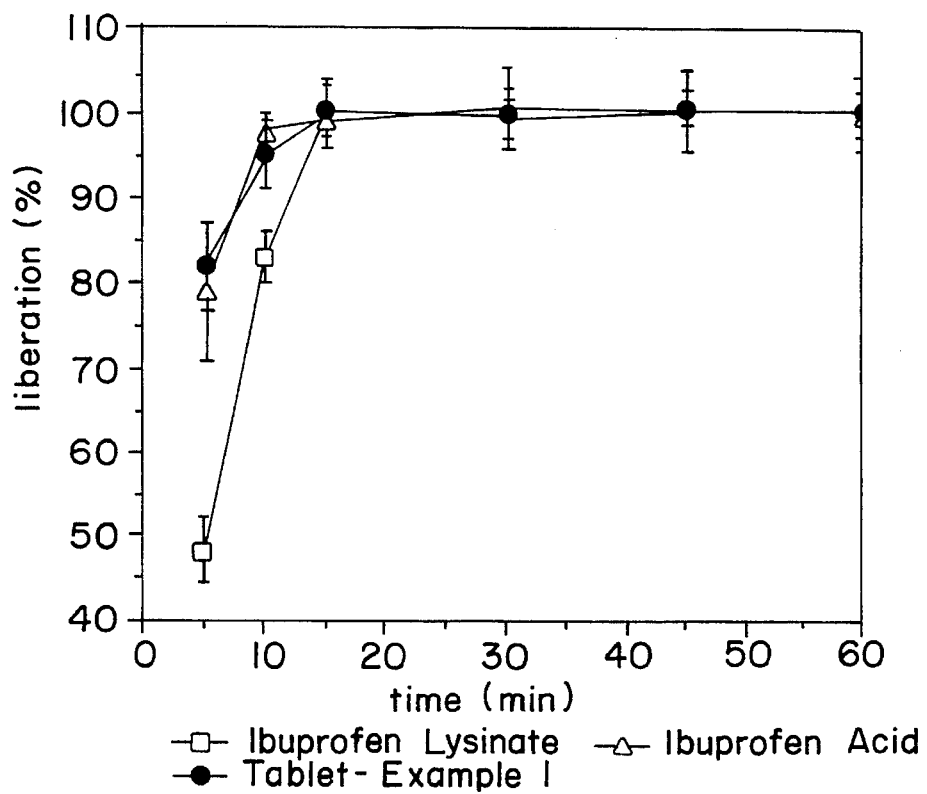
Figure 3:
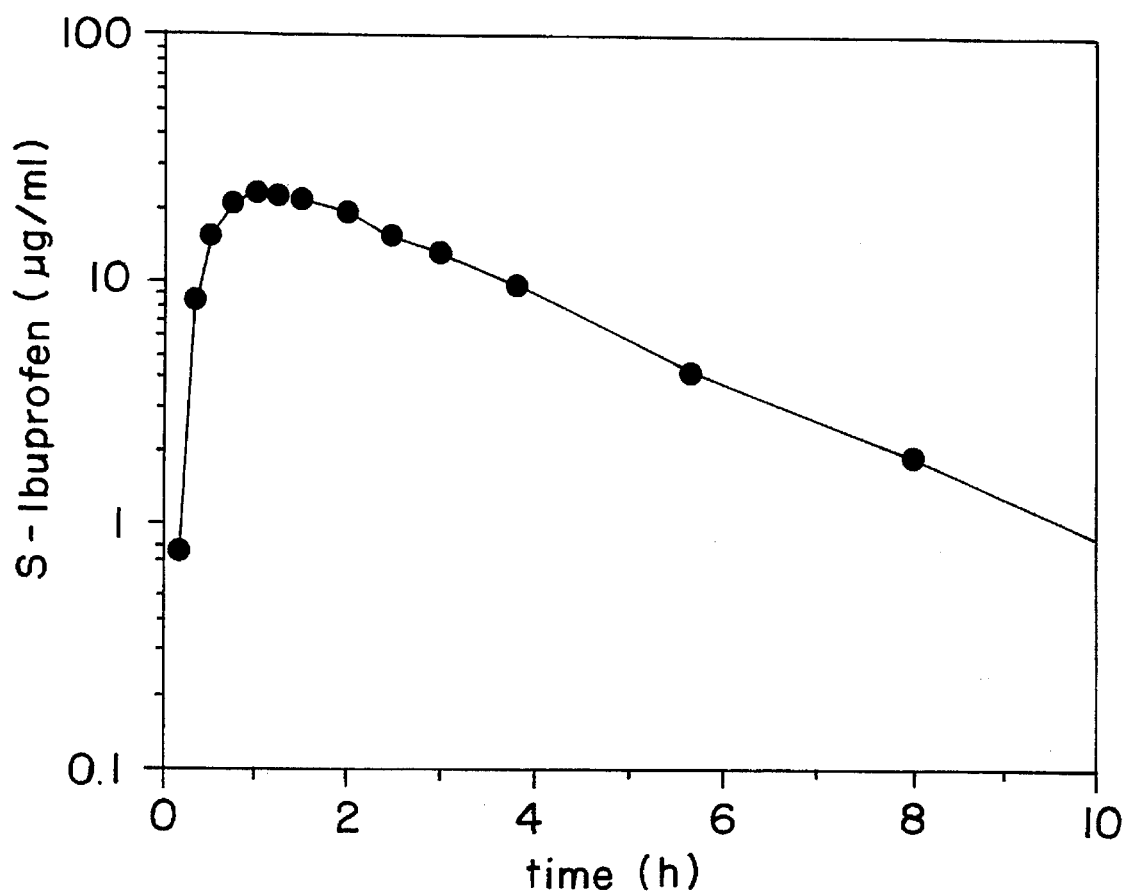
In FIG. 3 is illustrated the plasma concentration/course of time of S-ibuprofen after oral administration of a tablet according to the invention. The curve shows that these tablets correspond to the pharmacokinetic requirements.

S- and R-ibuprofen tablets
1 tablet contains:

| | |
|---|---|
| S-ibuprofen (about 99% optical purity) | 100 mg |
| R-ibuprofen (about 99% optical purity) | 50 mg |
| Emcompress | 140 mg |
| Explotab | 9 mg |
| Aerosil R 972 | 3 mg |

Production and properties as Example 1.

EXAMPLE 3

Ibuprofen racemate tablets
1 tablet contains:

| | |
|---|---|
| ibuprofen racemate | 300 mg |
| CaCO$_3$ | 210 mg |
| Explotab | 14 mg |
| Aerosil R 972 | 6 mg |
| Na lauryl sulphate | 3 mg |

Production as Example 1.

EXAMPLE 4

Ketoprofen capsules
1 capsule contains:

| | |
|---|---|
| S-ketoprofen (about 95% optical purity) | 50 mg |
| CaHPO$_4$ | 40 mg |
| Tween | 1 mg |
| Aerosil | 1 mg |

Filling of the dry mixed powder into hard gelatine capsules.

EXAMPLE 5

Flurbiprofen dragees

| | |
|---|---|
| R-flurbiprofen (about 98% optical purity) | 50 mg |
| Emcompress | 40 mg |
| Explotab | 4 mg |
| Aerosil R 972 | 2 mg |

Production analogous to Example 1.

The cores are subsequently costed according to known galenical formulations with a sugar solution to give the dragee.

We claim:

1. A process for the production of 2-arylpropionic acid derivative compositions having improved tablet forming characteristics, comprising:

(a) dry mixing one or more calcium compounds and one or more 2-arylpropionic acid derivatives into a powder mixture, thereby converting a small amount of the 2-arylpropionic acid derivatives into their respective calcium salts while retaining a substantially major part of the one or more arylpropionic acid derivatives in the acid form; and (b) pressing the powder mixture of (a) containing additionally one or more of an adjuvant or carrier material into one or more tablets, wherein substantially no conversion of the one or more 2-arylpropionic acid derivatives into a calcium salt occurs in the pressing.

2. A process according to claim 1, wherein the adjuvant comprises a pharmaceutically compatible wetting agent.

3. A process according to claim 1, wherein the one or more 2-arylpropionic acid derivatives comprises one or more of ibuprofen racemate and S-ibuprofen.

4. A process according to claim 1, wherein the one or more calcium compounds comprise one or more of $CaHPO_4$ and $CaCO_3$.

5. A process according to claim 1, wherein the pressing (b) are performed under dry conditions.

6. A process according to claim 1, wherein a calcium salt of the one or more 2-arylpropionic acid derivatives are present in an amount $\leq 5\%$.

7. A process according to claim 1, wherein the one or more 2-arylpropionic acid derivatives are present in an amount of 100 parts by weight and the one or more calcium compounds are present in an amount of 50–500 parts by weight.

8. A process according to claim 1, wherein substantially no lubricating agent or mold separation agent are present in the compositions.

9. A process according to claim 1, wherein approximately equimolar amounts of the one or more 2-arylpropionic acid derivatives and the one or more calcium compounds are present.

10. A process according to claim 1, further comprising (c) coating the one or more tablets.

11. A process according to claim 1, wherein the calcium salts of the one or more 2-arylpropionic acid derivatives are present in an amount to provide good tabletting properties without reducing the solubility of the composition.

12. A process according to claim 1, wherein the calcium salts of the one or more 2-arylpropionic acid derivatives are present in an amount of from 0.1 to 5%.

13. Process according to claim 2, characterized in that a pharmacuetically compatible wetting agent is used as adjuvant material.

14. Process according to claim 13, characterized in that $CaH(PO_4)$ or $CaCO_3$ is contained as calcium compound.

15. Process according to claim 14, characterized in that $CaH(PO_4)$ or $CaCO_3$ is contained as calcium compound.

16. Pharmaceutical composition according to claim 1.

17. Pharmaceutical composition produced according to claim 13.

18. Pharmaceutical composition produced according to claim 14.

19. Pharmaceutical composition produced according to claim 12.

* * * * *